United States Patent [19]
Manique et al.

[11] Patent Number: 5,523,560
[45] Date of Patent: Jun. 4, 1996

[54] METHOD AND APPARATUS FOR INSPECTING LIQUID-FILLED CONTAINERS

[75] Inventors: Flemming Manique, Ballerup; Tommy Martinussen, Slangerup; Gert Nielsen, Risskov, all of Denmark

[73] Assignee: Novonordisk A/S, Bagsvaerd, Denmark

[21] Appl. No.: 350,757

[22] Filed: Dec. 7, 1994

Related U.S. Application Data

[63] Continuation of Ser. No. 90,146, filed as PCT/DK92/00032, Jan. 30, 1992, published as WO92/14142, Aug. 20, 1992, abandoned.

[30] Foreign Application Priority Data

Feb. 1, 1991 [DK] Denmark .................................. 0177/91

[51] Int. Cl.$^6$ ............................. G01N 9/04; G06M 7/00
[52] U.S. Cl. ..................... 250/223 B; 250/576; 356/427; 209/526
[58] Field of Search .......................... 250/223 B, 227.11, 250/573, 576; 356/341, 342, 344, 237, 239, 240, 427, 343; 209/526, 577

[56] References Cited

U.S. PATENT DOCUMENTS

| | | | |
|---|---|---|---|
| 3,598,907 | 8/1971 | Drinkuth et al. | 178/178 |
| 3,777,169 | 12/1973 | Walter et al. | 250/218 |
| 3,880,750 | 4/1975 | Butler et al. | 250/223 B |
| 4,095,904 | 6/1978 | Klein et al. | 356/197 |
| 4,136,930 | 1/1979 | Gomm et al. | 358/106 |
| 4,274,745 | 6/1981 | Takahashi et al. | 356/427 |
| 4,605,851 | 8/1986 | Ometz et al. | 250/223 |
| 4,835,110 | 5/1989 | Seymour et al. | 356/341 |
| 5,141,609 | 8/1992 | Sweedler | 356/344 |

FOREIGN PATENT DOCUMENTS 0293510  12/1988  European Pat. Off. .

*Primary Examiner*—Stephone Allen
*Attorney, Agent, or Firm*—Steve T. Zelson; James J. Harrington

[57] ABSTRACT

The present invention relates to a method and apparatus for inspecting entities comprising liquid-filled containers for one or more test parameters of the liquid, the container, or both, by rotating and axially line scanning said entities and comparing said scans electronically, after which entities exhibiting one or more unacceptable test parameters are identified and separated from entities exhibiting acceptable test parameters.

25 Claims, 6 Drawing Sheets

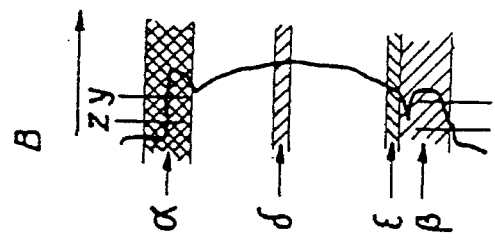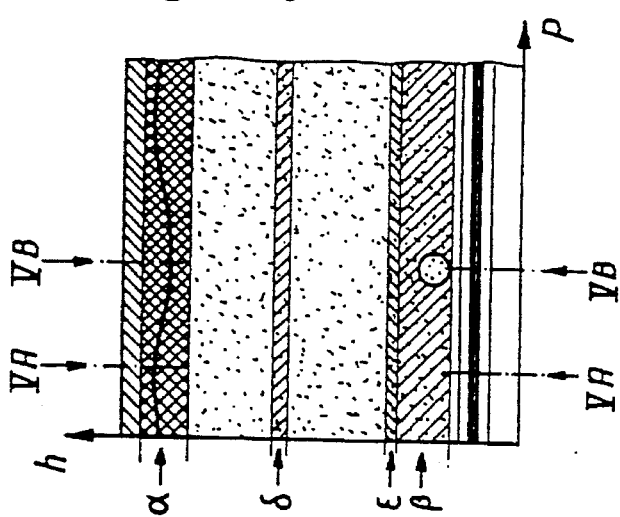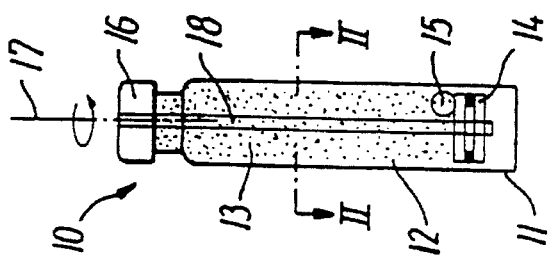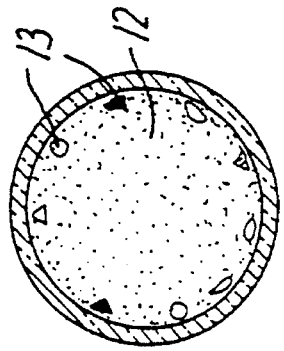

METHOD AND APPARATUS FOR INSPECTING LIQUID-FILLED CONTAINERS

This application is a continuation application of co-pending application Ser. No. 08/090,146, filed Sep. 7, 1993, now abandoned which is a continuation of PCT/DK92/00032, filed Jan. 30, 1992, the contents of which are incorporated herein by reference.

BACKGROUND OF THE INVENTION

1. Field of the Invention

The present invention relates to a method and apparatus for inspecting entities comprising liquid-filled containers for one or more test parameters of the liquid, the container, or both, by rotating and axially line scanning said entities and comparing said scans electronically, after which defective entities, i.e. entities for which one or more test parameters fall outside the approved ranges are identified and separated from non-defective entities, i.e. entities for which all test parameters fall within the approved ranges.

Generally, the method and apparatus for inspecting liquid-filled containers for rejection or approval according to the present invention is useful in e.g. the quality control of cartridges or vials containing liquid pharmaceuticals or other liquids.

Particularly, a method and apparatus for reliable inspection of several test parameters simultaneously including both stationary and dynamic type parameters of the entity to be inspected, i.e. the liquid, the container, or both, is of particular value in fast control of large batches of entities particularly when a high throughput, a high probability of rejecting defective entities, and a low probability of rejecting non-defective entities is required.

In the present context the expression, "line scanning" is intended to designate the collection of information from a line of segments on the container, including information from the liquid, the container, or both, each individual segment being scanned successively using a selfscanning linear CCD array. Lines of segments may be axial or non-axial related to the axis of rotation of the entity to be inspected depending on the relationship between the rate of rotation and the scanning rate of individual segments.

Also, within the present context the expression, "test parameters" is intended to designate measured parameters which reflect the quality of each entity to be inspected in such a way that their outcome results in either rejection or approval of the inspected entity. Examples of test parameters are parameters for detection of unacceptable defects such as dirt and cracks; amount of liquid, presence of air, concentration of solutes, presence of foreign particles and bodies, and the like.

Further, within the present context the expression "stationary parameters" is intended to designate parameters that do not change during rotation, e.g. parameters that are associated with the container such as the shape of the container, the cap, the amount of liquid, etc. Inspection of these parameters is designated "container inspection". The expression "dynamic parameters" is intended to designate parameters that change during rotation, e.g. parameters that are associated with movable foreign bodies such as suspended particles and impurities in the liquid. Inspection of these parameters is designated "foreign body detection".

2. Prior Art Disclosure

Methods and apparatus for inspecting liquid-filled containers for various parameters are known. However, to the applicant's knowledge, no prior art document discloses a method or an apparatus that performs a combined inspection of parameters, stationary or dynamic, by rotating the entity to be inspected according to a predetermined rate profile and simultaneously line scanning the entity axially.

U.S. Pat. No. 3,598,907 discloses object inspection by successively televised images wherein successive images of a rotating object are compared electronically to generate an error signal whenever the difference between successive images does not fall within a predetermined range. Also, U.S. Pat. No. 3,777,169 discloses a method and means based on rotation for detecting foreign particles in liquid-filled containers by means of a video camera capable of generating several video voltage patterns or frames.

Generally, these prior art apparatus suffer from a number of disadvantages. In particular, the apparatus are based on a video or analog sensing mechanism such as a conventional television camera which usually generates a surplus of data. Also, the frame rate of a television camera is very low (20 Hz) which creates aberration of a fast rotating particle and results in low sensitivity.

U.S. Pat. No. 4,136,930 discloses a method and apparatus based on rotation for a high-speed in-line bottle inspection apparatus comprising several television cameras for detecting foreign particles in full bevarage containers moving along a conveyor. Besides foreign particle detection the apparatus may be used for detecting proper fill levels of containers, detecting the proper content of pallets or cases for warehouse control, container identification, bottle sorting and other optical comparisons of which none are disclosed. However, besides the above mentioned drawbacks of known television camera based apparatus, the accuracy of detection is reduced due to electrical differences and misalignment errors between the cameras placed at different places in space and images obtained at different times.

German Laid-Open Application No. 2820661 A1 discloses a foreign body detection apparatus based on rotation that is independent of the particle con-figuration but which does not provide for other test parameters. Further, this known apparatus uses a collimated light source and detector apparatus for projecting the particle onto the sensor. Thus, this technique is not applicable for light-scattering liquids such as suspensions or emulsions in which cases the probability of rejecting defective entities becomes unacceptable low.

Thus, besides not being able to combine reliable detection of both stationary and dynamic parameters, all the above mentioned prior art techniques fail to provide reliable foreign body detection in non-transparent liquids such as suspensions or emulsions. In these cases, the incident light may not penetrate very far into the liquid and thus detection of foreign bodies in the bulk of a suspension or an emulsion is not achieved with prior art techniques.

Further, none of the above prior art techniques of inspecting liquid-filled containers discloses a method or an apparatus suitable for inspection of one or more test parameters of the liquid, the container, or both, simultaneously at a very high throughput having a high probability of rejecting defective containers and a low probability of rejecting non-defective containers.

SUMMARY OF THE INVENTION

Accordingly, it is the primary object of the present invention to provide a method and apparatus for inspecting entities comprising liquid-filled containers, particularly liquid-filled containers containing non-transparent liquids such as suspensions or emulsions, for one or more test parameters of e.g. dirt, cracks, false or foreign liquid, presence of air on top of the liquid, concentration of solutes or disperse phase, and foreign bodies like suspended particles and impurities; particularly inspecting such entities at a high throughput with a high probability of rejecting defective entities and a low probability of rejecting non-defective entities, after which inspection entities with unacceptable test parameters are identified and separated from entities with acceptable test parameters.

Further, it is another object of the present invention to provide a method and an apparatus for inspecting liquid-filled containers for one or more parameters of foreign bodies having various sizes and having densities higher than the liquid.

A method for inspecting liquid-filled containers

Surprisingly, these objects are fulfilled by providing a method of inspecting a liquid-filled container for one or more test parameters of the liquid, the container, or both, which method comprises rotating and axially line scanning said liquid-filled container, while it is rotated according to a predetermined rate profile and simultaneously line scanned axially, the scanned data being analysed.

Therefore, in its broadest aspect, the invention provides a method and an apparatus for simultaneously inspecting an entity comprising a liquid-filled container for one or more test parameters of the liquid, the container, or both, wherein the entity is rotated according to a predetermined rate profile and simultaneously submitted to axial line scanning, the data recorded during the scanning being analysed.

Thus, in container inspection according to the invention, said analysis of scanned data comprises image analysis of the unfolded image consisting of scans of the desired part of the surface of the container, and in foreign body inspection, according to the invention, said analysis of scanned data comprises analysis of successive scans of the contents of the container.

Within the present context, the expression "unfolding" is intended to mean the construction of a two-dimensional representation of one-dimensional line scans of the container. Thus, an unfolded image of stationary parameters may comprise an electronic representation of pixel values obtained from individual line scans during one or more 360 degrees revolutions of the rotating container, i.e. one dimension of the image being the height and the other the perimeter of the container; and an unfolded image of dynamic parameters may comprise an electronic representation of pixel values obtained at different times, i.e. the one dimension of the image being the height of the container and the other the time at which the same individual segment of the container was scanned.

In another aspect, the invention provides a method of inspecting an entity comprising a liquid-filled container for one or more test parameters of the liquid, the container, or both, wherein the entity is rotated and axially line scanned, the inspection comprising at least any sequence of:

a) rotating the entity according to a predetermined rate profile optionally having one or more periods of constant angular velocities, line scanning the container, and comparing pixel values of said line scans; and b) rotating the entity according to a predetermined rate profile having rates of rotation causing the liquid to circulate and foreign bodies having densities higher than the liquid to accumulate at the container wall, line scanning the entity, digitally filtering the pixel values of said scans, and comparing the filtered values with predetermined references.

(a) Stepwise or continuous rotation

In order to provide an unfolded image of the required resolution and quality for the test parameter to be inspected according to the invention, an unfolded image of the container may be provided by rotating the container either stepwise or continuously according to a predetermined rate profile which optionally has one or more periods of constant angular velocities during the inspection, and scanning the rotating container at a suitable scanning rate.

In a preferred embodiment, the rotation is chosen to be stepwise such that each individual segment of the container can be scanned for a sufficiently long time to provide the required resolution of the unfolded image. Thus, for a given rate of stepwise rotation and an appropiate scanning rate of the detection apparatus, a whole line of segments parallel to the axis of rotation may be scanned within an incremental step of the angular rotation.

In another embodiment, non-parallel e.g. helix type scanning may be applied to unfold a container image at relatively higher rates of rotation provided each individual scanned segment of the container can be unambiguously retrieved.

Rotation for stationay images

For stationary images, or container inspection, rates of angular rotation and scanning rates of the detection apparatus are chosen such that line scans are provided at relatively low rates and such that each individual segment of the container may be scanned once or several times through successive revolutions to provide several unfolded images.

In a preferred embodiment optional periods of constant angular velocity generally occur at rotation rates below 2000 rpm, particularly below 1500 rpm, preferably about 1200 rpm.

(c) Rotation for dynamic images

For dynamic images, i.e. foreign body detection, rates of angular rotation and scanning rates of the detection apparatus are chosen such that line scans may be provided at relatively high rates of rotation of the entity to be inspected. During these high rates of rotation line scans are provided differentially such that individual segments are scanned successively at given hights during one or more revolutions.

According to the invention, the rate profile comprises rates of rotation that causes the liquid to circulate and bodies having densities larger than that of the liquid to accumulate at the container wall. Thus, even for nontransparent suspensions and emulsions, foreign bodies at the container wall can be detected.

In a preferred embodiment detection of foreign bodies in the liquid having densities larger than that of the liquid is performed while the liquid is rotating at a rate from about 10000 rpm to about 2000 rpm, preferably from about 9000 rpm to about 7000 rpm, most preferred about 8000 rpm.

In still another embodiment the rotation of the container is stopped and the entity is scanned before the rotation of the liquid is substantially reduced.

Further, in another embodiment the total inspection time, including the scanning, is less than 1000 ms, preferably less than 500 ms, most preferred about 250 ms.

Within the present context, the expression "differentially" is intended to designate differentially in time or differentially in distance. Thus, for a circulating liquid contained in a container at rest, line scans may be provided "differentially in time" for given segments of the container by successive measurements of the same container segments but different segments of the rotating liquid. Also, for a rotating container, line scans may be provided "differentially in distance" for different segments of the perimeter by successive measurements of different container segments at different times.

(d) Irradiation and detection

In a preferred embodiment the entity is irradiated with electromagnetic radiation and the transmitted, reflected, diffracted or scattered radiation is detected at an angle from about 90 to about 180 degrees, preferably about 120 degrees, relative to the incident radiation.

In another preferred embodiment the transmitted, reflected, diffracted or scattered radiation is retro-reflected into the direction opposite of the incident radiation.

Further, in still another embodiment the retro-reflected radiation is reflected out of the incident direction by means of a semi-transparent and reflecting mirror.

In a preferred embodiment the transmitted, reflected diffracted or scattered radiation is detected by a linear array of radiation dectors and stored digitally, preferably in a frame store memory and a matrix filter.

According to the invention, analysis of recorded data comprises electronic comparison of actual pixel values or manipulated pixel values, e.g. values of individual pixels or values of groups of pixels that may be transformed by multiplication, addition, subtraction, or other transformations such as logaritms, means and standard deviations. Thus depending on the test parameter to be inspected, individual pixels, i.e. pixel addresses, are chosen and their values applied for the comparison.

Thus, in preferred embodiments individual pixels and groups of pixels are selected to analyse recorded data of one or more test parameters of the liquid and the container, respectively.

(e) Test parameters

In a preferred embodiment one or more test parameters of the liquid is selected from the group consisting of:

type of liquid, including clear solution, emulsion, and suspension;

liquid specification, including amount and intended content, concentration of components, colour, transmittance, and mixer ball; and foreign matter, including foreign liquids and bodies, suspended particles, impurities and undesired flocculation, growth of crystals and biological organisms.

Further, in a preferred embodiment one or more test parameters of the container are selected from the groups consisting of:

container specification, including shape, bottom, cap, labels, bar code, plunger, fill level, colour and transmittance;

container defects, including flaws, cracks, air bubbles and particles entrapped in the container wall, and weakenings; and container contamination, including dirt and dust, material entrapped between the plunger and container wall.

(f) Identification and separation of unacceptable containers

In a preferred embodiment, an inspected entity exhibiting one or more unacceptable test parameters of the liquid, the container, or both is identified and separated from containers having acceptable test parameters.

Apparatus for inspecting liquid-filled containers

Further, to fulfill the above objects, the invention provides an apparatus for inspecting an entity comprising a liquid-filled container for one or more test parameters of the liquid, the container, or both, by rotating and axially line scanning said container which may be liquid-filled, i.e. the entity to be inspected, and comparing said scans electronically comprising rotating means, irradiating means, detection means, and electronic digital filtering and comparison means.

(a) Means of rotation

Means of rotating the entity to be inspected comprise any means suitable for effecting either stepwise or continuous rotation. Presently a micro-processor controlled stepper motor stepping a predefined incremental angle of rotation synchronically with the scanning of the container is preferred.

A presently preferred program comprises accelerating the entity to be inspected until a first constant rate of rotation at which the container and liquid are inspected for stationary parameters, said rate of rotation having a constant angular velocity. Depending on the scanning rate of the detection means and the required resolution, this inspection is performed at rotation rates generally below 2000 rpm, particularly below 1500 rpm, preferably about 1200 rpm. Further, the program comprises rotating, e.g. accelerating or decelerating, the entity to be inspected to a second, or optionally a third, a fourth, and so on, rate of rotation at which the container and liquid may be inspected for dynamic parameters, e.g. foreign bodies.

It is preferred that the rotation of the container is stopped prior to inspection for dynamic parameters of the liquid. Thus presently preferred rate profiles comprise intervals during which the liquid continues to circulate while the container is at rest. Accordingly, the micro-processor is programmed to decelerate the rotation of the container generally in less than 500 ms, particularly less than 100 ms, preferably in the range 20–80 ms.

Accordingly, in a preferred embodiment, rotation means comprise a programmable stepper motor, preferably a low inertia stepper motor, programmed to provide a predefined rate profile over the total time of inspection and to stop the rotation generally in less than 500 ms, preferably in less than 100 ms, particularly in the range of 20–80 ms.

It is contemplated that the stopping of the container during the scanning for dynamic parameters is unnecessary when the influence of mechanical vibrations and oscillations of the container wall is reduced by incorporation of an optical retro-reflector means in the detection apparatus.

In the case of suspensions or emulsions being inspected, it is generally preferred to shake or agitate the container prior to rotation, e.g. by rotating the container about an axis perpendicular to the axis of rotation, or by contacting the container with a vibrator.

(b) Means of irradiation

According to the invention, the inspection apparatus comprises means of irradiating the entity to be inspected by a suitable electromagnetic radiation of any suitable wavelength acceptable to the liquid and container, and means for detecting the transmitted, reflected, diffracted or scattered radiation.

In a preferred embodiment, the irradiation means comprises:

a) a dc-powered light source, or a synchronized stroboscobic light source, preferably a stabilized tungsten light source;

b) an IR-filter removing radiation having a wavelength longer than approximately 1000 nm; and c) fiber optical light guides, preferably glass fibers, arranged in a long narrow line of width approximately 1.0 mm and of length corresponding to the full axial length of the container.

(c) Means of detection

In a preferred embodiment the transmitted or scattered radiation from the irradiated entity to be inspected is detected by detection means comprising an optical lens imaging the transmitted or scattered radiation, from preferably a narrow, e.g. 50 µm wide, vertical line segment of the container, onto a linear array of imaging photodetectors containing anywhere from 32 to 10000 elements, preferably a linear CCD- or PCCD-array having 1024 pixels of 14×14 µm, i.e. CCD-devices (charge coupled devices), or PCCD-devices (programable charge coupled devices). Particularly preferred devices are linear CCD- or PCCD-arrays of high resolution.

Further, the detection means comprise means for line scanning the pixels of the CCD-array serially, i.e. accessing the radiation sensitive elements sequentially, preferably every 200 µs, and by an analog video processing transforming an analog pixel value to a digital representation to be stored in a frame store memory or manipulated otherwise e.g. by digital filtering.

In a preferred embodiment the detection means further comprises means for transforming the analog pixel value to a digital value.

Colour recognition may be applied via the use of colour-CCD linescanners having optical interference filters integrated directly on the line-scan CCD sensor chip. Therefore, in another preferred embodiment, three trigger controlled stroboscobic light sources are used each filtered for a red, green and blue output, and all feeding their output into the same fibre bundle guiding light to the container to be inspected. Three successive line-scans with respectively the red, green and blue sources illuminating the container facilitates a full colour image to be gathered, giving colour information on both the container and its contents.

(d) Means of digital filtering and comparison

According to the invention line scans are compared via comparison of actual or manipulated pixel values which comparison may be obtained by suitable electronic digital filtering and comparison means known per se.

It is preferred that means of digital filtering comprises a digital matrix filter having filter coefficients loadable from software which matrix filter can be in the form of integrated circuits, or consist of conventional electronics comprising e.g. cascade shift registers, multipliers, substractors, accumulators, etc. known to a person skilled in the art.

Further, it is preferred that electronic comparison means comprises a frame store memory known per se which memory is computer controlled to store a complete unfolded image of the entity to be inspected, and the data of which may be processed by an image processing computer.

In a preferred embodiment the electronic comparison means comprises a digital matrix filter and/or a frame store memory.

Retro-reflection

According to the present invention, distinction between dynamic parameters of the liquid and static parameters of the container wall can be provided by stopping the rotation of the entity to be inspected and scanning the entity while the liquid is still rotating at an almost unchanged predetermined rate. However, for entities to be inspected for stationary parameters only or entities having recognizable known dynamic parameters like trapped air bubbles of given sizes, stopping of the rotation of the container may be avoided.

Therefore, according to the present invention the optical inspection apparatus can further comprise retro-reflection means to reflect the transmitted and scattered radiation retro-reflectively, approximately along the same path as the incident radiation but in the opposite direction. Under these conditions, the vibrating or oscillating movements as well as the distribution of the refractive index in both the container wall and the liquid can be considered static within the propagation time of the incident and retro-reflected light.

Liquids and liquid-filled containers

According to the invention, a "liquid-filled container" to be inspected may comprise any container that is transparent to the electromagnetic radiation applied; particularly preferred transparent containers are cartridges, ampoules, vials, and capsules, produced from materials normally intended for containing pharmaceutical liquids, e.g. glass or plastic.

Within the present context the expression "liquids" designates any liquids, mixtures, solutions, suspensions, colloidal dispersions, emulsions, etc., organic or inorganic; particularly pharmaceutical liquids comprising micro'suspensions such as insulin. Further, within the present context the expression "inspection" designates the acts of inspecting an object for certain predefined quality assurance parameters for example in order to comply with rules of good manufacturing practice and warrants of products.

Test parameters

The test parameters for containers are not restricted to "presence of" or "absence of", but generally comprise a reproducible measurement that can be calculated from the unfolded image, the result being compared to the tolerance allowed for the particular test parameter, and subsequently used for an accept/reject decision. Similarly when inspecting labels, text recognition can be applied to ensure correct labeling.

Contrary to prior art technique that applies different inspection means for inspection of stationary and dyna-mic parameters of liquid-filled containers, the present invention provides the possibility of applying a single line scanning apparatus for both classes of parameters. This possibility is surprisingly achieved through the combination of rotation schemes, according to the invention, and the line scanning apparatus providing for an unfolded image of the container and its contents.

Means of identification and rejection of containers obtaining unacceptable test parameters.

According to the invention, entities that have been inspected for one or more test parameters may be identified as unacceptable when a test parameter turns out to be outside the predefined range for acceptable values.

Accordingly, in a preferred embodiment of the present invention, the inspection apparatus further comprises means of identifying unacceptable entities. Thus identification of unacceptable entities can be based on the output signals of the digital filtering and comparison means, e.g. the output of the digital matrix filter or the output of the image processing computer having processed the data of the frame store memory.

Further, in a preferred embodiment, the inspection apparatus comprises means for separating entities identified as unacceptable from approved entities. In one aspect of the invention such means of rejecting unacceptable entities comprises electronic and mechanical means of separating said unacceptable entities from accepted entities.

When an entity is rejected the computer may store information about the type of parameter on the basis of which the rejection took place, thereby making it easier for the operator to identify the reason for a possible rise in the number of rejections.

Other objects and further scopes of application of the present invention will become apparent from the detailed description.

It should be understood that the detailed description and specific examples are only illustrations indicating preferred embodiments of the invention, and that various changes and modifications are possible without deviating from the spirit and scope of the present invention as apparent to those skilled in the art.

BRIEF DESCRIPTION OF DRAWINGS

FIG. 1 shows a liquid-filled container to be inspected according to a preferred embodiment;

FIG. 2 shows a cross-section along the line II—II of FIG. 1;

FIG. 4 shows an unfolded image of the container shown in FIG. 1;

FIG. 5A illustrates the pixel values along the line VA—VA in FIG. 4;

FIG. 5B illustrates the pixel values along the line VB—VB in FIG. 4;

Figure 3A:
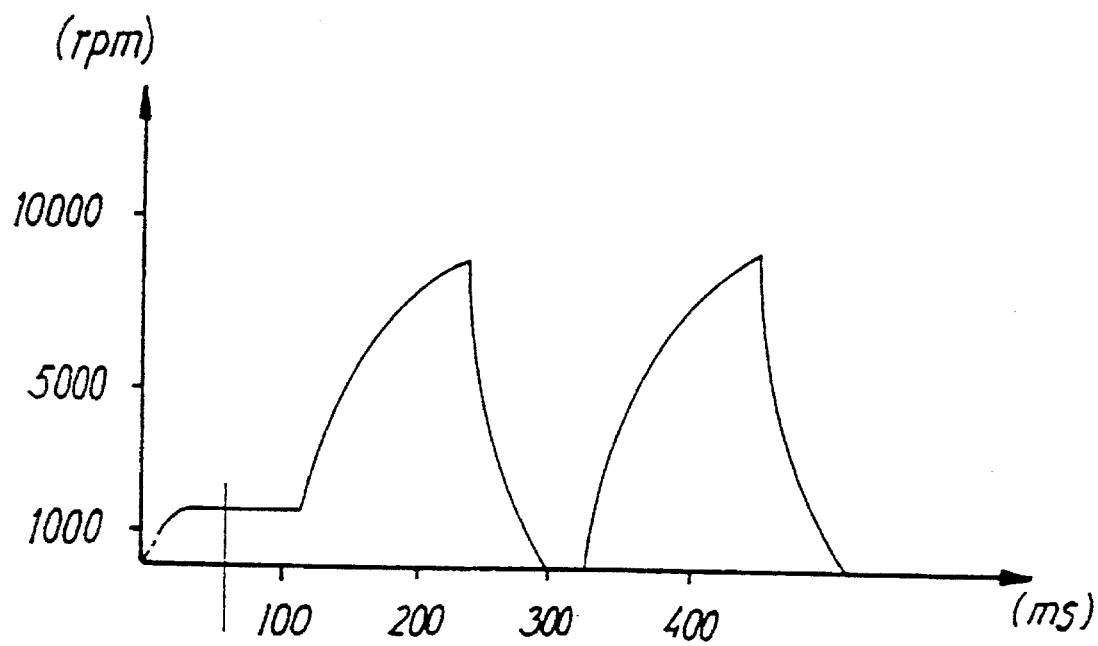
FIGS. 3A–D show examples of rate profiles of the rotation.

DETAILED DESCRIPTION AND PREFERRED EMBODIMENTS (a) Liquid-filled container

Referring to FIG. 1, there is illustrated a liquid-filled cylindrical container 10, e.g. an insulin cartridge, comprising a container body 11 and a suspension 12 in which foreign bodies 13 may be distributed. Further, the container contains a plunger 14, a mixer ball 15, and a rubber membrane (not shown) fixed to the container by means of a cap 16. During rotation, the entity to be inspected 10 is rotated about its longitudinal axis of rotation 17 and inspected in a linear field of inspection 18 which covers the desired section of the entity to be inspected.

(b) Foreign body distribution

Referring to FIG. 2, there is illustrated a cross-section along the line II—II of FIG. 1 illustrating the foreign bodies 13 accumulated and rotating in a well-defined manner close to the container wall at the time of inspection. Contrary to this, prior art techniques inspect for randomly distributed foreign bodies 13 not rotating close to the container wall, and thus are only applicable for transparent liquids.

(c) Rate profiles

Referring to FIGS. 3A–D, there are shown examples of rate profiles which illustrate the presently preferred continuous rate profiles.

In FIG. 3A, the container is accelerated until a predetermined constant rate of rotation is obtained, as illustrated by the plateau. At this constant rate of rotation line scans for container inspection are performed. Then, the entity to be inspected is accelerated to higher rates of rotation until a maximum value, after which the acceleration of the container is stopped and the container is decelerated before differential line scanning for detection of foreign bodies in the liquid. Acceleration for an optional repetition of the differential line scanning may follow immediately, or later, e.g. in another optical configuration.

Figure 3B:
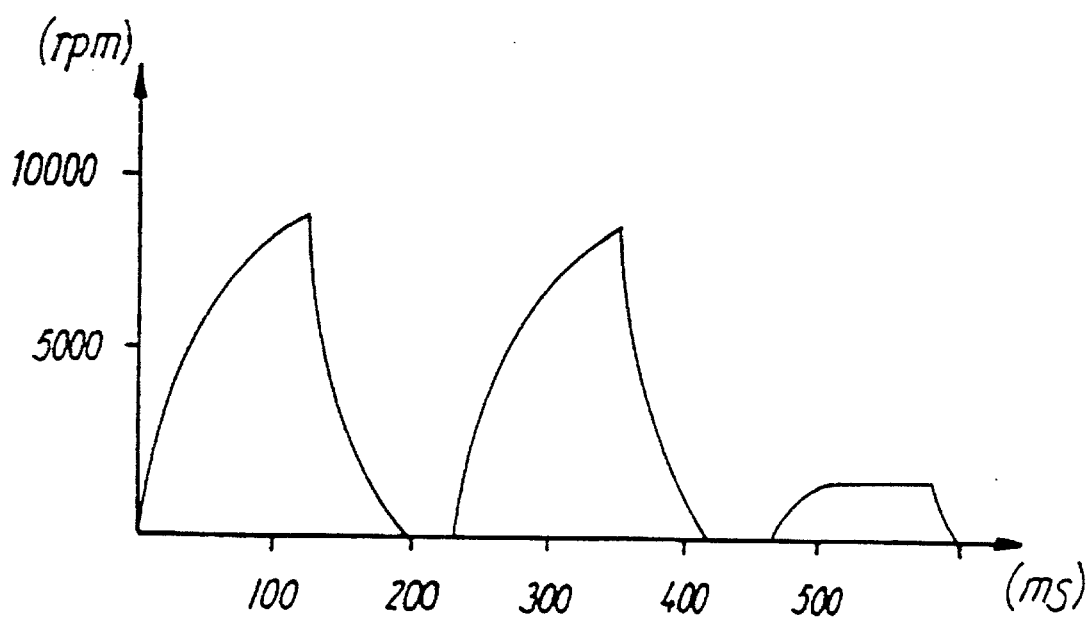

In FIG. 3B, the rotation for differential line scanning is provided, and may be repeated, before the container inspection is performed, i.e. the sequence of FIG. 1A is inverted. Also, for certain applications either the container inspection or the foreign body detection may be performed alone or in any other suitable sequences.

Figure 3C:
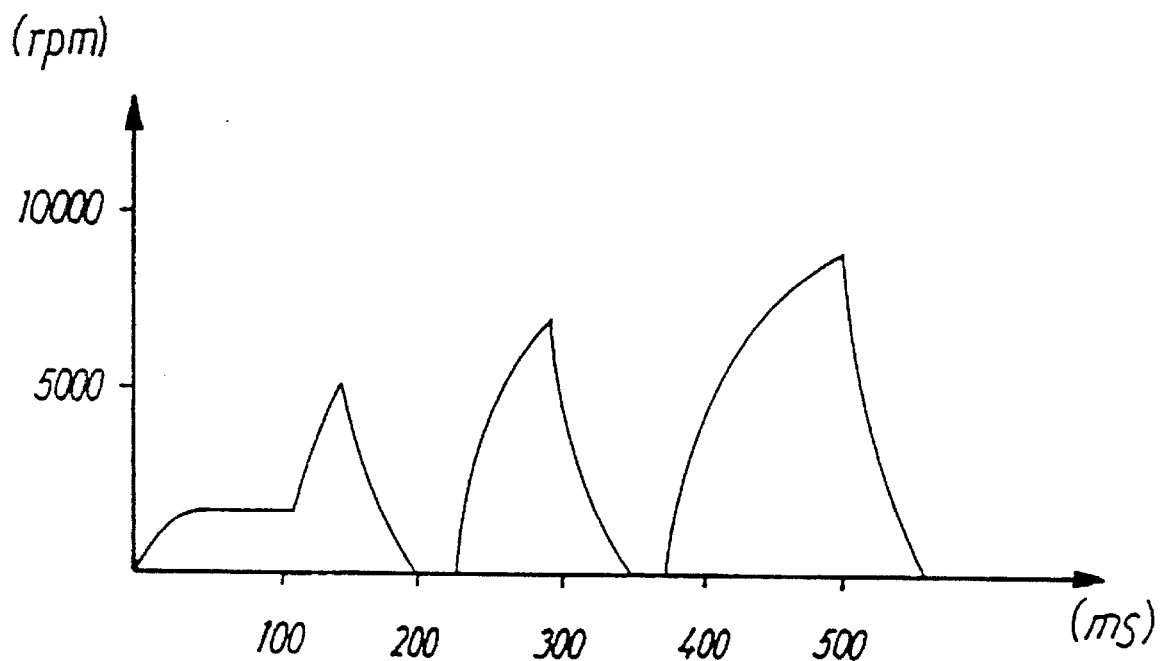

In FIG. 3C, the sequence of foreign body detection is provided at different maximum rates of rotation in order to differentiate between foreign bodies e.g. bodies of different size, shape, or density.

Figure 3D:
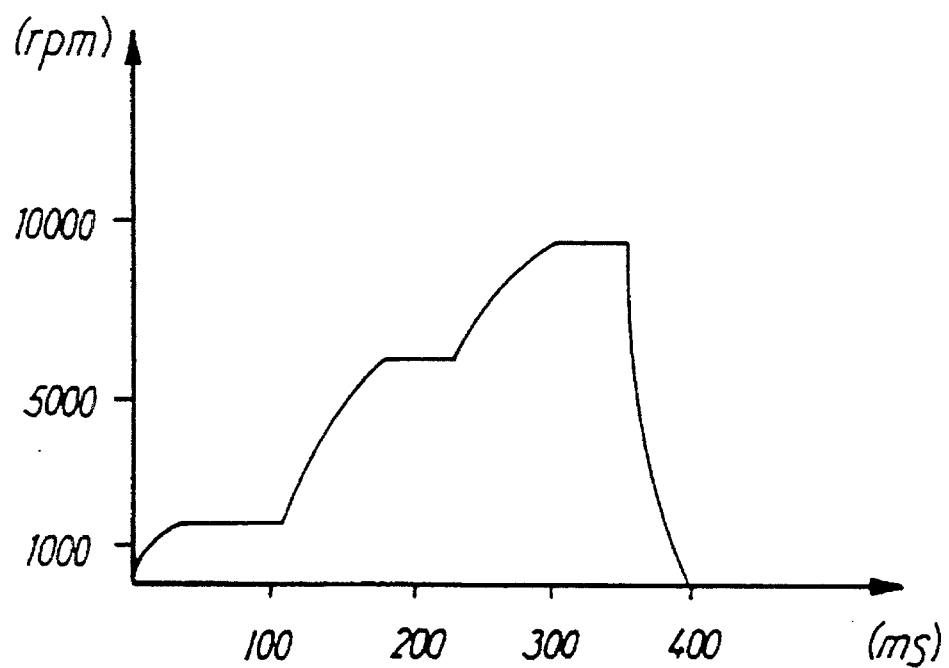

Finally, FIG. 3D illustrates a rate profile applicable for a apparatus based on retro-reflection of the transmitted and scattered radiation, in which case the rotation is not stopped between repeated inspections for foreign bodies.

(d) Image analysis of unfolded stationary images

Referring to FIG. 4 and FIG. 5, axial line scanning of the liquid-filled container successively at different angles of rotation provides a two-dimensional unfolded image representation of the container. FIG. 4 shows the two-dimensional projection of the unfolded image of the container shown in FIG. 1 with the height h of the container along the ordinate and the perimeter p as shown enlarged corresponding to the angle of rotation along the abscissa. For each coordinate, there is an associated pixel value.

In FIG. 5A and FIG. 5B, the pixel values are illustrated for given perimeters A and B corresponding to the scans along the lines VA—VA and VB—VB of FIG. 4.

In a preferred embodiment, image analysis is based on inspection windows $\alpha, \beta, \delta$ og $\epsilon$ that are defined as showed in FIG. 4 in order to provide container inspection for e.g. skewness of the cap, presence of the mixer ball, and air under the cap.

In a preferred embodiment, the threshold X is defined as as 90% of the full signal; the threshold Y is defined as a portion of a reference R1 determined as the mean of all pixel values within the window $\delta$; and the threshold Z as a portion of a reference R2 determined as the mean of all pixel values within the window $\epsilon$.

Thus, skewness of the cap can be detected by comparing for each line scan the pixels of the window G with the threshold Z starting from the cap. When Z is exceeded, the height is stored in a memory, and comparison of the minimum and maximum heights of all scans provides a measure of the skewness of the cap. Thus, for unacceptably large differences, the container may be rejected.

For the detection of air under the cap, the transmission of the liquid may increase, and the threshold X may be exceeded. Summing up all pixel values may provide a measure of the projected area of air.

In the presence of a transparent mixer ball, e.g. of glass, the transmission through the window $\beta$ may increase. Thus, the total mixer ball area projected can be measured by summing up all pixel values within the $\beta$-window that exceed the Y-threshold. The distinction between none, one or more mixer balls is then provided by a criterion which is based on the area ranges provided by the corresponding number of mixer balls.

Other test parameters of both the liquid and the container may be defined according to these principles, e.g. the concentration of a suspension may be determined by numerical intregration of the pixel values shown in e.g. FIG. 5A-excluding the "air peak", and/or the plunger position, and possible skewness of the plunger may be measured using the same procedure as described above for the cap using an appropriate reference and threshold. Also, the plunger position, e.g. the surface facing the liquid, identified as the height (i.e. the pixel number) at which the corresponding pixel value exceeds the threshold Z may be used to check the positioning of the plunger.

(e) Apparatus for inspecting liquid-filled containers

Figure 6:
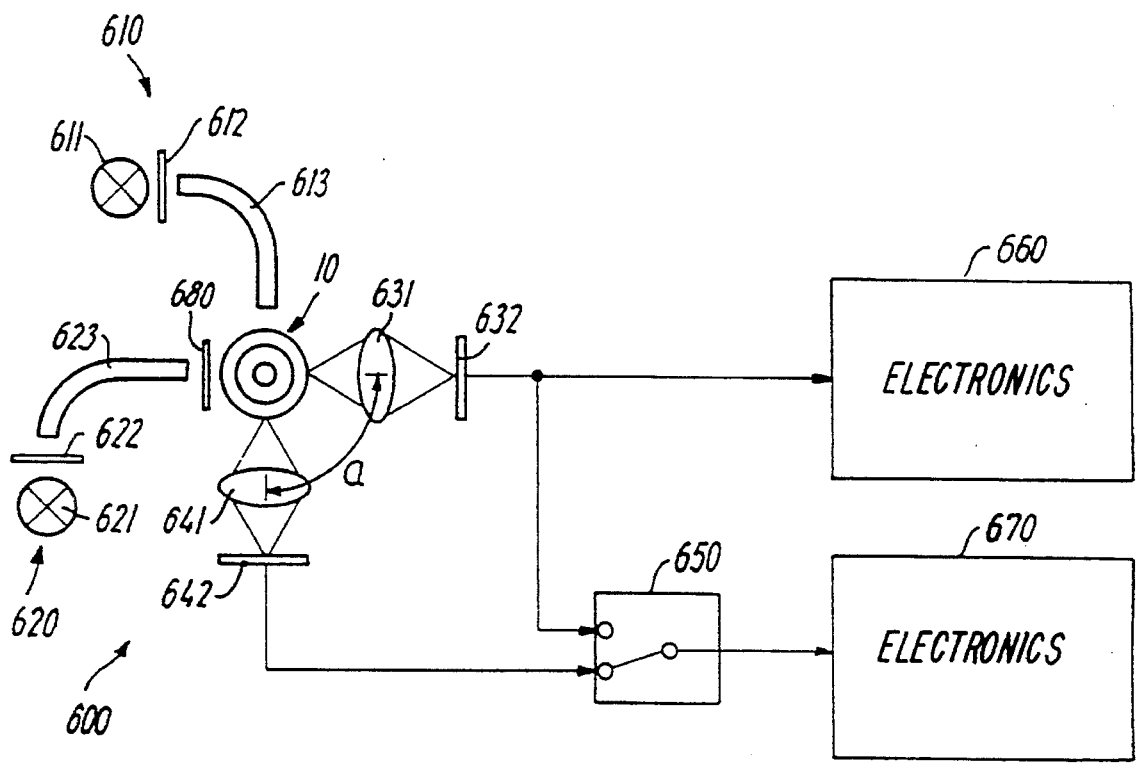
FIG. 6 shows a diagram of a setup according to a preferred embodiment for container inspection and particle detection.

Referring to FIG. 6, a preferred embodiment, 600, of the apparatus for inspecting both the container and its contents is illustrated. Two identical light apparatus 610 and 620 having stabilized dc-powered tungsten light sources 611, 621, infra red filtres 612, 622, and fiber optical light guides having cross-sectional converters 613, 623 are provided for. For non-transparent liquids only light apparatus 610 is applied. The switch 650 is in the position providing foreign body detection by collecting lenses 631, 641, detection means 632, 642 and part of the electronics 660 (see FIG. 7A), and part of the electronics 670 (see FIG. 8). For transparent liquids, both light apparatus 610 and 620, and detection means 632 and 642 may generally be applied with the switch 650 in the position shown. Additionally, an external diffusor 680 may be necessary between the light apparatus 620 and the container 10 particularly for transparent liquids.

In a simpler setup which provides more limited possibilities for the container inspection, the light apparatus 610, the collecting lense 641, and the detection means 642 are omitted, and signals from the detection means 632 are routed to the electronics for both the container inspection and foreign body inspection by the switch 650.

Further, the inspection apparatus comprises a low inertia stepper motor 705 (see FIG. 7A and FIG. 8), e.g. an Escap P42.

(f) Foreign body detection and electronics

FIG. 7A and 7B illustrate a preferred embodiment of an apparatus, 700, for inspecting e.g. a suspension-filled container for dynamic parameters. Particularly, FIG. 7A illustrates the foreign body detection part of the electronics.

In FIG. 7A, light from a stabilized dc-powered tungsten lamp 611 is filtered through an infra red filter 612 for removal of wavelengths longer than aproximately 1000 nm. Via a fiber optical light guide 613 the filtered light is directed to a cross-sectional converter 614 converting a circular cross-section to a rectangular cross-section. The output geometry of the converter 614 is provided by a glass fiber bundle confined in an aluminium block and has a width of about 1.0 mm and a height corresponding to the height of the entity 10 to be inspected. The converter 614 can be provided with collimator and aperture means. Normally, for the inspection of suspensions or emulsions, the light guide output is directed towards the entity to be inspected at an angle of 90 to 120 degrees relative to the optical axis of the imaging apparatus, i.e. a collecting lense 631 and a detection means 632, e.g. a linear array such as Toshiba TCD 107, as shown in top view in FIG. 7B. However, alternative configurations and angles may be applied depending on the specific liquid to be inspected.

Further, the apparatus 700 comprises a low inertia stepper motor 705 for rotating the entity to be inspected. This motor can very rapidly accelerate the entity to be inspected to high rates of rotation and decelerate the rotation within a very short time. Thus, the deceleration from about 9000 rpm to zero can take place in less than 60 ms. Any solids in the container such as foreign bodies, particles, or a mixer ball having a density larger than the liquid will accumulate at the inside of the container wall. The extremely short deceleration time ensures that the circulating liquid continues its rotation in a circular laminar flow during the inspection of the liquid immediately after the container has stopped its rotation. A longer deceleration time would result in the flow breaking into a turbulent flow which would cause said foreign bodies to move into the bulk of the liquid before the container had stopped and thus become undetectable. Also, in the case of transparent liquids, foreign bodies moving into the bulk of the liquid may come out of the focus of the optics, and thus may not be detected.

The electronics part of the apparatus comprises an analog video processing board 708 containing circuitry to accept unprocessed analog pixel values from the detection means 632 and transform it to a series of digital pixel data, each represented by an 8 bit word. A CCD or PCCD sequencer board 709 comprises high-speed high current drivers, clocks and sequencing electronics familiar to a person skilled in the art to facilitate a high pixel rate (5 MHz) without sacrificing precision in the restoration of the analog pixel information. A high-speed stepper motor controller 710 provides a high rate of rotation of the entity 10 to be inspected, e.g. 9000 rpm, and a very precisely controlled deceleration of the container within a short time, e.g. less than 60 ms, for foreign body detection of the liquid. For container inspection, the controller 710 provides an accurate and precise rate of rotation of e.g. about 1200 rpm. A main controller 711 provides the actions necessary to inspect the liquid for foreign bodies and other irregularities. Also, the controller 711 and the analog video board 708 provides control signals (A) and (B), respectively, to the electronics part for container inspection (see FIG. 8).

Especially, the electronics for detection of foreign bodies form a universal digital matrix filter, where filter coefficients are loadable from software. This facilitates setting filter characteristics, which will enable detection of foreign bodies circulating in the suspension with maximun sensitivity, without being disturbed by the likewise circulating mixer ball. To the applicants' knowledge no other apparatus has this facility. Known apparatus would instead detect the mixer ball as being an undesired foreign body.

In one embodiment the digital matrix filter consists of cascade shift registers 712–716 having lenghts corresponding to the number of pixels in the linear array of the detection means 632. Thus, each register constitutes one full line scan having an 8-bit representation of the corresponding pixel value in each cell. Depending on the desired filter characteristics of the detection, a variable number of shift registers may be applied. Multipliers 717–721 provide multiplication of individual coefficients to the pixel values of the shift registers, which coefficients are loaded from the controller 711. A summing network 722 computes the sum of the results of multiplications by the multipliers 717–721 which multipliers may scale the s results depending on the dynamic behaviour of the fluid being inspected. A numerical subtractor 723 computes numerical differences between the summed output of the summing network 722 and the pixel value present at the output of 714. A threshold register 724, i.e. a loadable shift register to be loaded by the controller 711, contains one full line scan of threshold values. Each threshold value is clocked out of the register syncronically with the result of the numerical subtractor 723, and recycled into itself. The contents of the threshold register 724 is adaptable, and may depend on the shape of the curvature of the collecting lens 632, and optical aberrations from the glas container 10. A comparator 725 compares pixel thresholds of the threshold register 724 with the filtered pixel values of the numerical subtractor 723, and provides a logical outputsignal, when the numerical subtractor 723 provides a signal larger than the threshold register 724. A gate 726 controlled by the controller 711 determines that the output signal from the comparator 725 is valid, e.g. only when the rotation of the container has been stopped, and a certain predetermined time has elapsed, during which the liquid continues to rotate at a high rate.

In another embodiment, the digital matrix filter may consist of an integrated circuit, e.g. INMOS IMS A110.

Further, to increase the sensitivity of the foreign body detection several algoritms controlling the digital matrix filter, e.g. the filter coefficients, may be applied. Thus, each line scan of successive line scans can be filtered by more filters each optimized for detection of preferred types of foreign bodies, e.g. small, large, thin or thick particles consisting of glass, metal, or hair. For example, the signal of the register 715 may be routed to a second set of shift registers having another set of multipliers providing different individual coefficients to the pixel values.

(g) Container inspection and electronics

Figure 7:
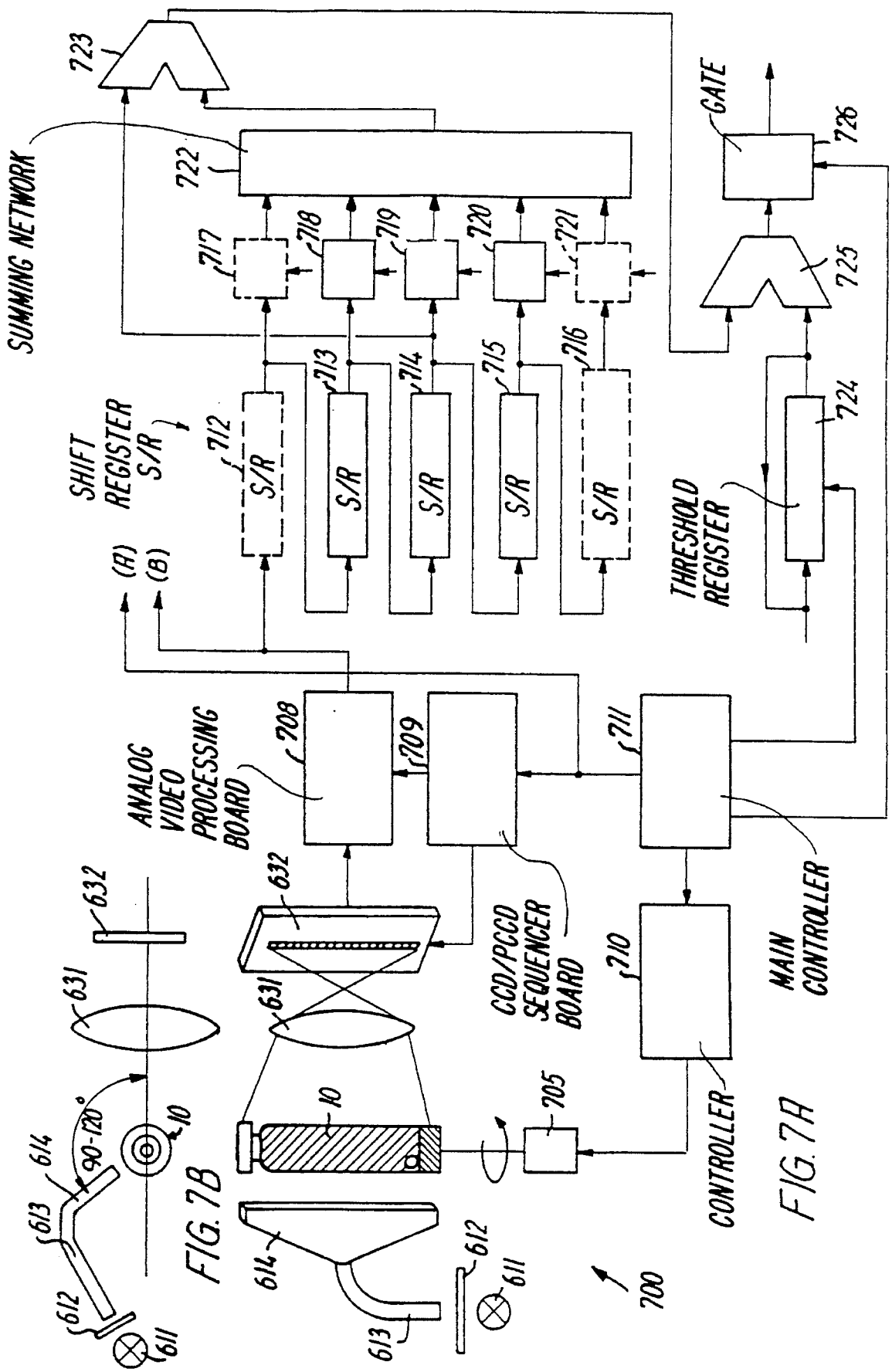
FIG. 7A shows a diagram of the apparatus for foreign body detection.
FIG. 7B shows a top view of a detail of the apparatus of FIG. 7A.
Figure 8:
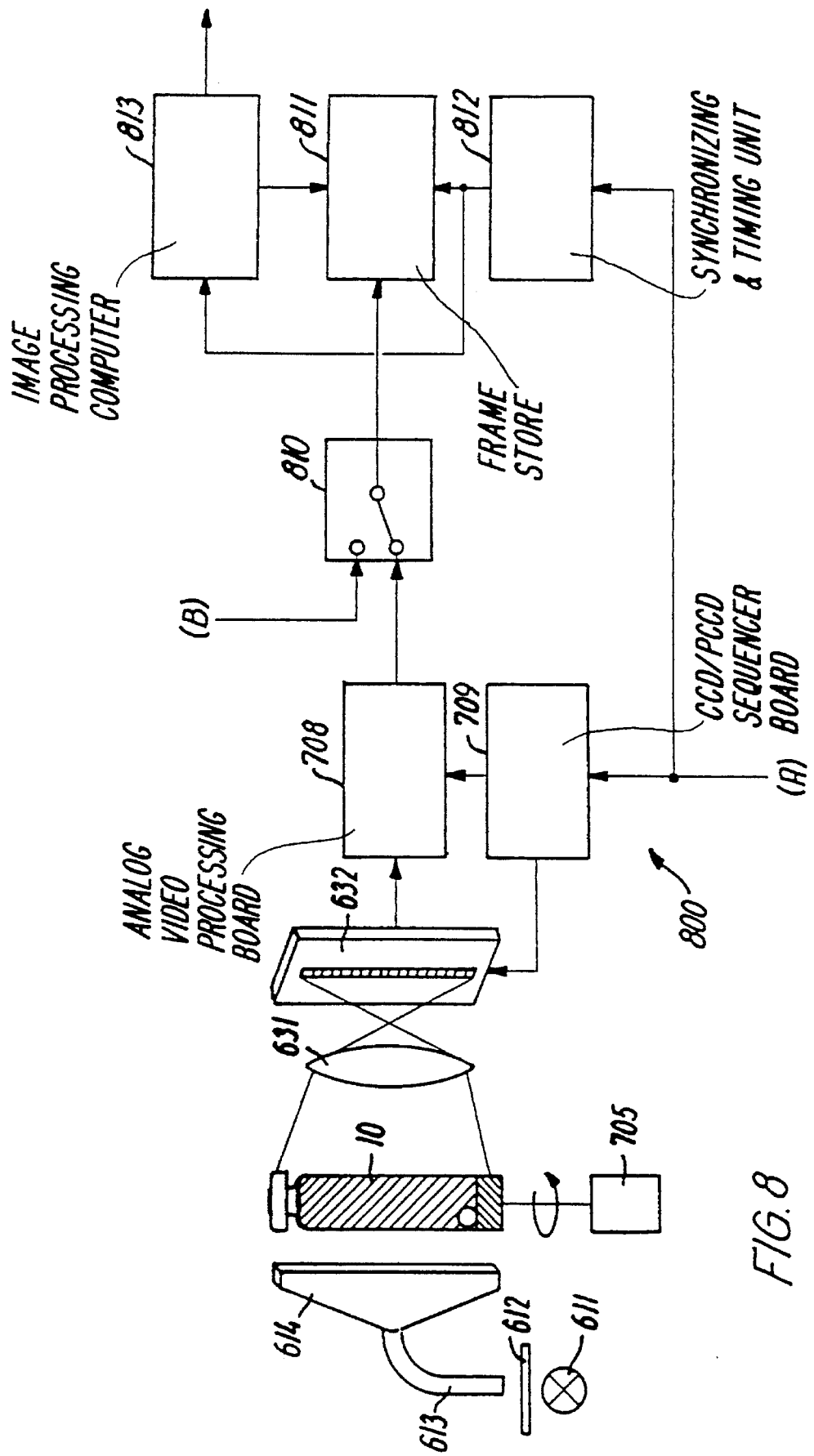
FIG. 8 shows a diagram of the apparatus for container inspection.

Referring to FIG. 8, there is illustrated a diagram of a preferred embodiment 800 of the apparatus of the electronics part for container inspection. Particularly, FIG. 8 illustrates the container inspection part of the electronics. Numerals 611–709 designate components which are similar to the components designated by the same numerals in FIGS. 6 and 7A.

In FIG. 8, the switch 810 selects the line scan depending on the optical configuration chosen as described for FIG. 6. Thus, line scans (B) from the optical configuration shown in FIG. 7A may be selected. A frame store 811, e.g. Scan Beam SB1024, is loaded with an unfolded image of the container to be inspected. The size and resolution of the stored image depends on the dimensions of the container and on the details inspected for. Generally, the number of rows in the frame store 811 is equal to the number of pixels of the linear array 632 whereas the number of columns depends on the inspection to be performed. Typically, however, the standard number of columns, i.e. from 128 to 1024 or higher, are used. The pixel values are stored as 8-bit words. A synchronizing and timing unit 812 receives input (A) from the controller 711 shown in FIG. 7A when the rate of rotation of the container has reached a predetermined level that is used for obtaining and loading a new image in the frame store 811. When the loading is completed, the image processing computer 813, which is programmed to perform the necessary processing on the image stored in the frame store 811, is informed that a new image is ready for processing. The result of the inspection is a signal for accepting or rejecting the entity to be inspected.

EXAMPLES

For testing the apparatus cylindrical cartridges were filled or partly filled with an insulin micro-suspension (50 μm particles), and intentionally provided with various defects of either the container or the liquid in order to simulate different defects, and subjected to container inspection and foreign body detection.

Example 1

Container inspection 60 cylindrical cartridges (1.5 ml, Penfill®) were divided into groups having the defects of added air, skew caps, or missing or additional transparent glass mixer balls as shown in Table 1.

The cartridges were subjected to container inspection at a rotation rate of 1200 rpm and line scanned to provide images of 1024 rows and 256 columns. The images were then analysed for the test parameters of skewness of the cap, air under cap, and presence of a transparent mixer ball. In all cases the different types of defects were detected correctly.

TABLE 1

| | Contents and defects | |
|---|---|---|
| Number | Contents *) | Defective |
| 7 | Insulin + 1 mixer ball | Skew cap |
| 11 | Insulin + 1 mixer ball | Air added |
| 11 | Insulin + no mixer ball | Mixer ball missing |
| 30 | Insulin + 2 mixer balls | More mixer balls |
| 1 | Insulin + 6 mixer balls | More mixer balls |

*) Insulin: insulin micro-suspension (50 μm particles)

Example 2

Foreign body detection 6 cylindrical cartridges containing one transparent glass mixer ball and artificial or natural particulate contamination were rotated to a rate of 8600 rpm, and stopped within 225 ms. The cartriges were then inspected for 350 ms in a 120 degrees backscatter setup with a 50 μm vertical pixel resolution, and a line-scan rate of 5000 scans/s using a clock frequency of 5 MHz. 2 cartridges with mould added and 4 cartridges with metal particles added were detected correctly in all cases.

Example 3

Foreign body detection/filter setting

For detection of foreign bodies having different characteristic as shown in Table 2, the filter matrix of a digital matrix filter, IMS A 110, INMOS, corresponding to the loadable filter coefficients for the multipliers 718–720 for the shift registers 713 of 715 of the digital matrix filter in FIG. 7 were varied according to Table 3.

TABLE 2

| Kind and dimensions of foreign bodies | | |
|---|---|---|
| Foreign body | Dimensions (mm) | Number |
| Glass particles | 0.5 × 0.5 | 1 |
| Glass particles | 1 × 1 | 1 |
| Glass particles | 3 × 2 | 1 |
| Hair | 0.02 × 3 | 1 |
| Hair | 0.04 × 8 | 1 |
| Hair | 0.05 × 4 | 1 |
| Hair | 0.1 × 10 | 1 |
| Hair | 0.1 × 15 | 1 |
| Metal thread | 0.3 × 15 | 1 |
| Metal particles | 0.15 × 0.15 | 6 |
| Metal particles | 0.7 × 0.7 | 2 |
| Metal particles | 0.7 × 0.7 | 7 |
| Metal particles | 0.9 × 0.9 | 6 |

40 cylindrical cartridges (3 ml) were filled with insulin micro-suspension (50 μm particles) and one transparent glass mixer ball was added to each cartridge. Further foreign bodies in the form of particles of glass, hair or metal were added to 3, 5 and 5 respectively of the cartridges as shown in table 2. All 40 cartridges were randomized and used for testing the foreign body detection function. Each cartridge was accelerated to a rate of rotation of 7000 rpm, stopped within 80 ms, and inspected in a 120 degrees backscatter setup with a 50 μm vertical pixel resolution, and a line scan rate of 5000 scans/s using a clock frequency of 5 MHz. Inspection for foreign bodies was repeated for each revolution of the cartridge.

The experimental parameters and results are shown in Table 3. The error-detection percentages obtained in the range 0.9–2.4% and average detection percentages in the range 84–90% are both significantly better than those of prior art and manual inspection schemes of comparable types of foreign bodies. Also, the results show that the signal from a transparent mixer ball can be reduced to insignificant levels by optimizing the filter setting.

TABLE 3

| | Experimental parameters and results | | | | | |
|---|---|---|---|---|---|---|
| A | B | C | D | E | F | G |
| 1 | 0, –1, 1 | 12 | 150 | 100 ms | 1.1% | 88% |
| 2 | 1, –2, 1 | 10 | 96 | 100 ms | 1.2% | 90% |
| 3 | 1, –2, 1 | 10 | 100 | 100 ms | 0.9% | 90% |
| 4 | 1, 1, 1<br>1, –8, 1<br>1, 1, 1 | 49 | 100 | 100 ms | 2.0% | 86% |
| 5 | 1, 0, 1<br>0, –4, 0<br>1, 0, 1 | 31 | 100 | 100 ms | 2.4% | 86% |
| 6 | 0, –1, 1 | 12 | 106 | 50 ms | 1.4% | 84% |
| 7 | 1, –2, 1 | 10 | 230 | 50 ms | 0.9% | 88% |

Legend: A: Experiment No.; B: Filter setting, i.e. filter coefficients for the matrix filter; C: Threshold value of register 724, i.e. a number in the range 0–255; D: Number of revolutions, i.e. repetitions; E: Inspection time; F: Error detection percentage, i.e. the percentage of nondefective entities erroneously detected as unacceptable entities (ideally zero); and G: Average detection percentage of defective entities.

We claim:

1. A method for inspecting an entity comprising a liquid-filled container for one or more test parameters of the liquid, the container, or both, wherein the entity is irradiated by irradiating means, rotated and axially line scanned along a line parallel with the axis of rotation by detecting means detecting radiation reflected, diffracted, or scattered from the entity, the inspection comprising at least one sequence of:

a) rotating the entity according to a predetermined rate profile having one or more periods of constant angular velocities, line scanning the container axially during the periods of constant angular velocities, and comparing pixel values of said line scans with set references; and b) rotating the entity according to a predetermined rate profile comprising rates of rotation causing the liquid to circulate and foreign bodies having densities higher than the liquid to accumulate at the container wall, bringing the container to a standstill with the liquid rotating, line scanning the entity axially before the rotation of the liquid is substantially reduced, digitally filtering the pixel values of said line scans, and comparing the filtered values with predetermined references.

2. A method according to claim 1, wherein the periods of constant angular velocity generally occur at rotation rates below 2000 rpm.

3. A method according to claim 2, wherein the constant angular velocity is about 1200 rpm.

4. A method according to claim 1, wherein the detection of foreign bodies in the liquid having densities larger than that of the liquid is performed while the liquid is rotating at a rate from about 10000 rpm to about 2000 rpm.

5. A method according to claim 4, wherein the liquid is rotating at a rate about 8000 rpm.

6. A method according to claim 1, wherein the total inspection time including the scanning, is less that 1000 ms.

7. A method according to claim 5, wherein the total inspection times, including the scanning, is about 250 ms.

8. A method according to claim 1, wherein said entity is irradiating with electromagnetic radiation and the transmitted, reflected, diffracted or scattered radiation is detected at an angle from about 90 to about 180 degrees relative to the incident radiation taken about the axis of rotation.

9. A method according to claim 8, wherein the transmitted, reflected, diffracted or scattered radiation is detected at an angle of 120° relative to the incident radiation taken about the axis of rotation.

10. A method according to claim 1, wherein the entity is irradiated with electromagnetic radiation, and the radiation reflected, diffracted or scattered into the direction opposite the incident radiation is detected as retroreflected radiation.

11. A method according to claim 10, wherein said retroreflected radiation is reflected out of the incidentdirection by means of a semi-transparent and reflecting mirror.

12. A method according to claim 8, wherein said transmitted, reflected, diffracted or scattered radiation is detected by a linear array of radiation detectors and stored digitally, preferably in a frame store memory and a matrix filter.

13. A method according to claim 1, wherein one or more test parameters of the liquid is selected from the group consisting of:

type of liquid, including clear solution, emulsion, and suspension;

liquid specification, including amount and intended content, concentration of components, color, transmittance, and mixer ball; and foreign matter, including foreign liquids and bodies, suspended particles, impurities and undesired flocculation, growth of crystals and biological organisms.

14. A method according to claim 1, wherein one or more test parameters of the container is selected from a group consisting of:

container specification, including shape, bottom cap, labels, bar code, plunger fill level, color and transmittance;

container defects, including flaws, cracks, air bubbles and particles entrapped in the container wall, and weakenings; and container contamination, including dirt and dust, material entrapped between the plunger and container wall.

15. A method according to claim 1, wherein an inspected entity exhibiting one or more unacceptable test parameters of the liquid, the container, or both, is identified and separated from containers exhibiting acceptable test parameters.

16. An apparatus for inspecting an entity comprising liquid-filled container for one or more test parameters of the liquid, the container (10), or both, by rotating, irradiating, and axially line scanning said entity and comparing said scans electronically, comprising rotating means (705) for rotating the entity according to a predetermined rate profile having one or more periods of constant angular velocities, and for rotating the entity to another predetermined rate profile comprising rates of rotation causing the liquid to circulate and foreign bodies having densities deities higher than the liquid to accumulate at the container wall and of bringing the container to a standstill, irradiating means (611–614), detection means (631–632), and electronic digital filtering comparison means (708–726).

17. An apparatus according to claim 16, wherein said rotation means (705) comprises a programmable stepper motor, preferably a low inertia stepper motor, programmed to provide a predefined rate profile over the total time of inspection and to stop the rotation generally in less than 500 ms, preferably in less than 100 ms, particularly in the range 20–80 ms.

18. An apparatus according to claim 16, wherein said irradiating means (611–614) comprises:

a) a dc-powered light source (611), or a synchronized stroboscopic light source, preferably a stabilized tungsten light source;

b) an IR-filter (612) removing radiation having a wavelength longer than approximately 1000 nm; and c) fiber optical light guides (613), preferably glass fibers, arranged in a long narrow line (614) of width approximately 1.0 mm and of a length corresponding to the full axial length of the container.

19. An apparatus according to claim 16, wherein said detection means (631–632) comprises an optical lens (631) imaging the transmitted or scattered radiation, from preferably a narrow, e.g. 50 μm wide, vertical line segment of the container, onto a linear array (632) of imaging photo detectors containing anywhere from 32 to 10000 elements.

20. An apparatus according to claim 19, wherein the linear array of imaging photo detectors is a linear CCD- or PCCD-array having 1024 pixels of 14×14 μm.

21. An apparatus according to claim 20, wherein said detection means further comprises means line scanning the pixels of the CCD- or PCCD-array serially.

22. An apparatus according to claim 20, wherein each pixel is accessed every 200 μs.

23. An apparatus according to claim 20, wherein said detection means further comprises means for transforming analog pixel values to digital values.

24. An apparatus according to claim 16, wherein said electronic digital comparison means comprises a digital matrix filter and/or a frame store memory.

25. An apparatus according to claim 16, further comprising means of identifying and means of separating containers having one or more unacceptable test parameters of the liquid, the container, or both, from containers having acceptable test parameters.

* * * * *